US006794344B2

(12) United States Patent
Taylor et al.

(10) Patent No.: US 6,794,344 B2

(45) Date of Patent: Sep. 21, 2004

(54) SOAP BARS EXHIBITING ANTIBACTERIAL EFFECTIVENESS AND METHOD OF PRODUCING SAME

(75) Inventors: Timothy Taylor, Phoenix, AZ (US); Ricardo Diez, Corona, CA (US); Michael Slayton, Woodstock, GA (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 10/300,266

(22) Filed: Nov. 20, 2002

(65) Prior Publication Data

US 2004/0097387 A1 May 20, 2004

(51) Int. Cl.$^7$ .................................................. A61K 7/50

(52) U.S. Cl. ....................... 510/141; 510/152; 510/153; 510/147; 510/155

(58) Field of Search ................................ 510/141, 152, 510/153, 147, 155, 130

(56) References Cited

U.S. PATENT DOCUMENTS

| | | | | | |
|---|---|---|---|---|---|
| 5,021,183 | A | * | 6/1991 | Saud | 252/108 |
| 6,007,831 | A | | 12/1999 | Fujiwara et al. | |
| 6,107,261 | A | | 8/2000 | Taylor et al. | |
| 6,255,265 | B1 | * | 7/2001 | Van Gunst et al. | 510/152 |
| 6,310,015 | B1 | | 10/2001 | Diez et al. | |
| 6,342,470 | B1 | * | 1/2002 | Aronson et al. | 510/153 |

* cited by examiner

*Primary Examiner*—Necholus Ogden
(74) *Attorney, Agent, or Firm*—Snell & Wilmer L.L.P.

(57) ABSTRACT

A soap bar that exhibits antibacterial effectiveness includes, by weight, at least about 45% soap having alkyl chain lengths of 8–10 carbon atoms, water, and free fatty acid such that the pH of a 10% aqueous solution of the soap bar is no greater than about 9.5.

34 Claims, No Drawings

SOAP BARS EXHIBITING ANTIBACTERIAL EFFECTIVENESS AND METHOD OF PRODUCING SAME

FIELD OF INVENTION

The present invention relates generally to soap bars exhibiting antibacterial effectiveness and methods of producing the same, and more particularly to soap bars including soap components exhibiting antibacterial properties.

BACKGROUND OF THE INVENTION

Antibacterial personal care compositions are known in the art. Especially useful are antibacterial cleansing compositions, such as soap bars, that typically are used to cleanse the skin and to destroy bacteria and other microorganisms present on the skin, especially the hands, arms, and face of the user. Antibacterial compositions are used, for example, in the health care industry, food service industry, meat processing industry, and in the private sector by individual consumers. The widespread use of antibacterial compositions indicates the importance that consumers place on controlling bacteria and other microorganism populations on skin.

Commercial soap bars conventionally comprise one or more "soaps", which, for purposes of describing this component of the soap bars of the present invention, has the meaning as normally understood in the art: monovalent salts of monocarboxylic fatty acids. The counterions of the salts generally include sodium, potassium, ammonium and alkanolammonium ions, but may include other suitable ions known in the art. The soap bars also may include optional adjuvant ingredients such as moisturizers, humectants, water, fillers, polymers, dyes, fragrances and the like to effect cleansing and/or conditioning for the skin of the user.

Typically, the soap components in conventional soap bars comprise salts of long chain fatty acids having chain lengths of the alkyl group of the fatty acid from about 12 carbon atoms to about 18 carbon atoms in length. The particular length of the alkyl chain(s) of the soaps is selected for various reasons, including cleansing capability, lather capability, costs, and the like. It is known that soaps of shorter chain lengths are more water-soluble (i.e., less hydrophobic) and produce more lather compared to longer chain length soaps. Longer chain length soaps are often selected for cost reasons and to provide structure to the soap bars.

To provide an antibacterial property to such conventional soap bars, it is generally necessary to add germicides or antibacterial agents to the soap bars. Thus, for example, bars containing antimicrobials such as triclosan (i.e., 2,4,4'-trichloro-2'-hydroxy-diphenylether) and triclocarbanilide are known. However, the addition of antibacterial agents to soap bars to achieve antibacterial effectiveness can add cost to the soap bars due to the cost of the antibacterial agents themselves and the added costs of production of the soap bars.

Accordingly, there is a need for soap bars that exhibit enhanced antibacterial properties that are separate and distinct from those properties of added antibacterial agents. The present invention addresses this long-felt but unresolved need.

SUMMARY OF THE INVENTION

While the way in which the present invention addresses these needs is addressed in greater detail below, in general, the soap bars in accordance with various aspects of the present invention exhibit antibacterial effectiveness due to the antibacterial properties of the soap components comprising the bars, separate and distinct from any added antibacterial active agents. Such soap bars have surprising antibacterial effectiveness at relatively short contact times compared to conventional soap bars that typically comprise soap compositions of salts having 12 to 18 carbon atoms.

In accordance with an exemplary embodiment of the present invention, a soap bar that exhibits antibacterial effectiveness is provided. The soap bar comprises, by weight at least about 50% soap having alkyl chain lengths of 8–10 carbon atoms, water, about 10% to about 30% hydric solvent, preferably about 20% hydric solvent, and free acid, preferably free fatty acid, such that the pH of a 10% aqueous solution of the soap bar is no greater than about 9.

In accordance with another exemplary embodiment of the present invention, a soap bar is provided that comprises, by weight, at least about 50% soap having alkyl chain lengths of 8–10 carbon atoms. The soap bar exhibits a log reduction against Gram positive bacteria of at least 3 after 30 seconds of contact at 40° C., as measured against *S. aureus.*

In a further exemplary embodiment of the present invention, a method of making a soap bar that exhibits antibacterial effectiveness is provided. The soap bar comprises, by weight, at least about 50% soap having alkyl chain lengths of 8–10 carbon atoms, and water. The process comprises combining a neutralizing agent and fatty acids having alkyl chain lengths of 8–10 carbon atoms to form a soap solution and manipulating the composition of the soap solution, if necessary, so that a pH of a 10% aqueous solution of the soap bar is no greater than about 9. The process further includes removing a portion of water from the soap solution, optionally adding adjuvant ingredients, and solidifying to form the soap bar.

DETAILED DESCRIPTION

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

In one exemplary embodiment of the invention, the soap bars comprise at least about 45%, and preferably about 50%, by weight, of salts of monocarboxylic fatty acids having alkyl chains of 8 carbon atoms (C8), or 10 carbon atoms (C10), or a mixture of salts having alkyl chains of 8 and 10 carbon atoms. Counterions of the salts may include sodium, potassium, ammonia and alkanolammonium ions, although sodium is generally the preferred counterion.

In yet a further embodiment of the invention, the soap bars comprise less than 1.5%, preferably less than 1%, by weight, of salts of monocarboxylic fatty acids having alkyl chains of 12 (C12) to 16 (C16) carbon atoms, as Applicants have found that, as the presence of such salts increases, the antibacterial effectiveness of the soap decreases. In a more preferred embodiment of the invention, salts of monocarboxylic fatty acids having alkyl chains of 12 to 16 carbon atoms are substantially completely absent from the soap bars of the present invention. As described in more detail below, the soap bars are formed to comprise a free acid content such that a 10% aqueous solution of a soap bar of the present invention has a pH no greater than about 9.5, preferably no greater than about 9. Not wishing to be bound by any particular theory, it is believed that the soap molecules formed in accordance with embodiments of the present invention provide more free monomers in solution than longer chain soap molecules. These monomers, in a more acidic environment, may disrupt the bacteria cell membrane, resulting in rapid cell death.

In accordance with further embodiments of the present invention, the soap bars comprise compositions which assist in the formation of solutions and/or prevent or reduce formation of dispersions. For example, in such embodiments, the soap bars comprise a hydric solvent, preferably about 10% to about 30% by weight, and most preferably oil the order of about 20% by weight. The hydric solvent may comprise any now known or hereafter devised solvent, for example, an exemplary hydric solvent includes propylene glycol.

In another exemplary embodiment of the invention, the soap bars may comprise minor amounts, preferably no more than 5% by weight, of salts of monocarboxylic fatty acids having alkyl chains of 18 (C18) or more carbon atoms to provide structure in the finished soap bars and prevent or retard disintegration of the soap bar on exposure to water.

In yet another exemplary embodiment of the invention, the soap bars may be formed using water-soluble polyhydric organic solvents. Polyhydric organic solvents suitable for use in producing soap bars in accordance with the various embodiments of the present invention include, but are not limited to, propylene glycol, dipropylene glycol, butylene glycol, ethylene glycol, 1,7-heptanediol, monoethylene glycols, polyethylene glycols, polypropylene glycols of up to 8,000 molecular weight, mono-C1–4 alkyl ethers of any of the foregoing, mixtures thereof, glycerine, and any sugar alcohol, such as, for example, sorbitol.

The soap bars in accordance with the present invention may also contain other optional adjuvant ingredients that are present in sufficient amount to perform their intended function and that do not adversely affect the antibacterial efficacy of the soap bar composition. Such optional ingredients typically are present, individually, from about 0% to about 2%, by weight of the soap bar, and, collectively, from 0% to about 10%, by weight of the soap bar.

Classes of optional ingredients may include, but are not limited to, dyes, fragrances, pH adjusters, chelating agents, preservatives, stabilizers, colorants, polymers such as synthetic high polymers, derivatives of natural polymers such as modified cellulosic polymers, gums, and the like, antibacterial active agents, and similar classes of optional ingredients known the art.

A process for making the soap bars in accordance with one exemplary embodiment of the present invention will now be described. The soap components of the soap bars may be manufactured by mixing a fatty acid or acids and at least one neutralizing agent in an open agitated reaction vessel at atmospheric pressure and heating to a temperature sufficient to melt the fatty acids, generally at least about 80° C. to 90° C. The fatty acids include monocarboxylic fatty acids having alkyl chain lengths of 8 carbon atoms (C8) or 10 carbon atoms (C10), or a mixture of such fatty acids. Suitable neutralizing agents for manufacturing of the soap bars of the present invention include caustic solutions, for example, sodium bases such as NaOH. The neutralizing agent neutralizes the fatty acids, forming salts of the fatty acids (i.e., "soaps"), such as for example, sodium, potassium, ammonia or alkanolammonium salts. The neutralizing agent may be added in an amount less than the amount of the neutralizing agent required to fully neutralize the fatty acids. In one exemplary embodiment of the invention, about 95% of the required amount of neutralizing agent needed to fully neutralize the fatty acids may be added. The temperature preferably is maintained above about 80° C. but below about 100° C.

Additionally, a hydic solvent, such as propylene glycol, may be added to the mixture. The mixture should comprise, preferably about 10% to about 30% hydric solvent by weight, and most preferably on the order of about 20% by weight. The hydric solvent may comprise any now known or hereafter devised solvent.

Optionally at this point, the mixture may be analyzed for free acid and the pH of the mixture manipulated accordingly. For example, the mixture may be titrated with NaOH using a pH indicator and, if necessary, the composition of the mixture may be manipulated so that a 10% aqueous solution of the resulting soap bar has a pH no greater than about 9. For example, if the pH is too acidic, more neutralizing agent may be added. Alternatively, if the mixture has a pH above about 9, more free fatty acids may be added to the composition. If free fatty acids are added, it is preferable that the free fatty acids have alkyl chains of 8 to 10 carbon atoms.

At this stage of the manufacturing process, the temperature of the reaction mixture may be raised to at least about 90° C., preferably from about 90° C. to about 100° C., to evaporate a desired amount of water. Alternatively, the water may be evaporated before addition of an additional neutralizing agent or free fatty acid as described above. In one embodiment of the invention, the soap bar comprises no more than 25% water. Preferably, the soap bar comprises no more than 20% water. More preferably, the soap bar comprises no more than 15% water. When a desired amount of water has been removed from the soap component, the soap component may be cooled, optional ingredients may be added to the soap component using conventional methods, and the resulting composition may be formed into soap bars, either by pouring the composition, in a molten state, into molds, or, alternatively, by forming soap bars using conventional amalgamation, milling, plodding and/or stamping procedures as is well known in the art.

In another exemplary embodiment of a process for manufacturing the soap bars in accordance with the present invention, the soap bars may be made with a solvent. In this embodiment, the above-described process may be used, except that a polyhydric solvent is initially added to the reaction vessel and heated to a temperature of about 70° C. to 80° C. The neutralizing agent is then added to the solvent before the addition of the fatty acids(s) to prevent formation of gels or lumps, which would increase manufacturing time. As described above, the neutralizing agent is added in an amount less than the amount of the neutralizing agent required to fully neutralize the later-added fatty acids. In one exemplary embodiment of the invention, about 95% of the required amount of neutralizing agent needed to fully neutralize the fatty acids is added. The fatty acids are then added to the mixture while the temperature is maintained above about 80° C. but below about 100° C. The process may then continue as described above with the optional analyzing step, optional water removal step, the addition of optional ingredients and the formation of the soap bars.

To evidence the antibacterial effectiveness of various formulations of the soap bars formed in accordance with the present invention, time kill suspension tests were conducted, whereby the survival of challenged organisms exposed to an antibacterial test formulation is determined as a function of time. In general, the time kill method is well known in the antibacterial products industry. In this test method, a diluted aliquot of the formulation is brought into contact with a known population of test bacteria for a specified time period at a specified temperature. The test composition is neutralized at the end of the time period, which arrests the antibacterial activity of the composition. The percent or, alternatively, log reduction from the original bacteria population is calculated. All testing is generally performed in triplicate, the results are combined, and the average log reduction is reported. The choice of contact time period is at the discretion of the investigator. Any contact time period can be chosen. Typical contact times range from 15 seconds to 5 minutes, with 30 seconds and 1 minute being typical contact times.

The bacterial suspension, or test inoculum, is prepared by growing a bacterial culture on any appropriate solid media (e.g., agar). The bacterial population then is washed from the agar with sterile physiological saline and the population of the bacterial suspension is adjusted to about $10^8$ colony-forming units per ml (cfu/ml). The table below lists the test bacterial cultures used in the following tests and includes the name of the bacteria, the ATCC (American Type Culture Collection) identification number, and the abbreviation for the name of the organism used hereafter.

| Organism Name | ATCC # | Abbreviation |
|---|---|---|
| *Staphylococcus aureus* | 6538 | *S. aureus* |
| *Escherichia coli* | 11229 | *E. coli* |

*S. aureus* is a Gram positive bacteria, whereas *E. coli* is a Gram negative bacteria.

EXAMPLE 1

In this example, five different formulations of soap bars were tested using the time kill suspension test method. Table 1 summarizes the compositions of three formulations, Formulations 1A, 1B, and 1C. Two formulations (Formulations 1A and 1B) were formed in accordance with various aspects of the present invention. The third formulation (Formulation 1C) was formed with soap having alkyl chain lengths not in accordance with various aspects of the present invention. These three formulations, with each of the components set forth in weight percent, are as follows:

TABLE 1

| | weight percent | | |
|---|---|---|---|
| | Formulation 1A | Formulation 1B | Formulation 1C |
| Propylene Glycol | 33.5 | 25.8 | 22.1 |
| NaC8 | 25.1 | 0 | 0 |
| NaC10 | 25.1 | 50.2 | 25.0 |
| NaC12 | 0 | 0 | 5.0 |
| NaC14 | 0 | 0 | 9.9 |
| NaC16 | 0 | 0 | 7.5 |
| NaC18 | 0 | 0 | 7.5 |
| Water | 16.3 | 24.0 | 23.0 |

These three formulations were also tested against a commercial soap bar having a mixture of approximately 80% tallow fatty acid soap and 20% coco fatty acid soap (Formulation 1D) and against a soap bar comprising a mixture of soaps and synthetic detergents (Formulation 1E).

The five different formulations were tested using 10% aqueous solutions of the formulations. Each solution was added to a beaker in a water bath, stirred, and heated to approximately 40° C., which is typically the temperature at which consumers use soap bars for body cleansing. The solution then was inoculated with 1.0 ml of the test bacteria suspensions. The inoculum was stirred with the solution for a contact time of 30 seconds and 1 minute. When the contact time expired, 1.0 ml of the solution/bacteria mixture was transferred into 9.0 ml of Tryptone-Histidine-Tween Neutralizer Solution (THT). Decimal dilutions to a countable range then were made. Plate selected dilutions were produced in triplicate on TSA+ plates (TSA+ is Trypticase Soy Agar with Lecithin and Polysorbate 80). The plates then were incubated for 25+2 hours, and the colonies were counted for the number of survivors. The control count (numbers control) was determined by conducting the procedure as described above with the exception that THT was used in place of the test composition. The plate counts were converted to cfu/ml for the numbers control and samples, respectively, by standard microbiological methods.

The log reduction was calculated using the formula:

Log reduction=log10 (numbers control)−log10(test sample Survivors).

The following table correlates percent reduction in bacteria population to log reduction:

| % Reduction | Log Reduction |
|---|---|
| 90 | 1 |
| 99 | 2 |
| 99.9 | 3 |
| 99.99 | 4 |
| 99.999 | 5 |

The log reduction or, alternatively, the percent reduction, in bacterial populations provided by the antibacterial composition correlates to antibacterial activity. A log reduction of 3–5 is most preferred, a 1–3 reduction is preferred, whereas a log reduction of less than 1 is least preferred, for a particular contact time. Thus, a highly preferred antibacterial composition exhibits a 3–5 log reduction against a broad spectrum of microorganisms in a short contact time.

Table 2 summarizes the results of time kill tests performed on the solutions of the five formulations at 30 seconds and 1 minute contact times:

TABLE 2

| | Log Reduction at 30 sec/1 minute contact time | |
|---|---|---|
| Formulation | *S. aureus* | *E. coli* |
| 1A | >4.23/>4.23 | >4.88/>4.88 |
| 1B | 3.07/3.83 | >4.88/>4.88 |
| 1C | 2.73/3.26 | >4.88/>4.88 |
| 1D | 2.85/3.63 | 0.92/3.99 |
| 1E | 2.96/3.98 | 0.50/0.85 |

The above results illustrate the enhanced antibacterial effectiveness of soap bars formed in accordance with various embodiments of the present invention. At contact times of 30 seconds, Formulations 1A and 1B exhibited superior antibacterial effectiveness against *S. aureus* compared to Formulation 1C, Formulation 1D, and Formulation 1E. Both Formulations 1A and 1B exhibited log reductions of between 3 and 5, while the other formulations exhibited log reductions of only between 2 and 3. Formulation 1A, which comprised a mixture of NaC8 and NaC10 soaps, exhibited particularly good antibacterial effectiveness, with a log reduction of between 4 and 5. Similarly, Formulations 1A and 1B exhibited superior antibacterial effectiveness against *E. coli* compared to Formulation 1D and Formulation 1E. Both Formulations 1A and 1B exhibited log reductions of between 4 and 5, while the other two formulations exhibited log reductions of less than 1. The antibacterial effectiveness against *E. coli* of Formulation 1C was the same as Formulations 1A and 1B.

At contact times of 1 minute, the difference in antibacterial effectiveness against *S. aureus* of the five bars was less significant. However, the antibacterial effectiveness of Formulation 1A, which comprised a mixture of NaC8 and NaC10 soaps, again exhibited superior antibacterial effectiveness against *S. aureus* compared to the other soap bars, with a log reduction of between 4 and 5. With respect to *E. coli*, Formulations 1A and 1B again exhibited enhanced antibacterial effectiveness, with log reductions of between 4 and 5. The antibacterial effectiveness of Formulation 1C was comparable. The antibacterial effectiveness of Formulations 1A and 1B (and 1C) were better than that of Formulation 1D bar, which exhibited a log reduction below 4. The antibacterial effectiveness of Formulations 1A and 1B were far superior to that of Formulation 1E, which exhibited a log reduction of less than 1.

EXAMPLE 2

Further testing was conducted to compare the antibacterial effectiveness of soap bars formed in accordance with various aspects of the present invention with soap bars that do not have the free fatty acid content contemplated by various aspects of the present invention. Four different formulations of soap bars were tested with the time kill suspension test method described above using an *S. aureus* test inoculum. Formulations 2A and 2C comprised 28.8% NaC8, 28.2% NaC10, 33.5% propylene glycol and the balance water. Formulations 2B and 2D comprised 28.8% NaC8, 28.2% NaC10, 33.4% propylene glycol and the balance water. However, two formulations (Formulations 2A and 2C) were formed in accordance with various aspects of the present invention, that is, these soap bars were formed to comprise an amount of free fatty acid such that the pH of a 10% aqueous solution of the soap bars was no greater than about 9. The two remaining formulations (Formulations 2B and 2D) were formed to comprise an amount of free fatty acid such that the pH of a 10% aqueous solution of the soap bars was greater than 9. The testing was conducted at two different temperatures, 25° C. and 40° C., with a contact time of 30 seconds.

Table 3 summarizes the results of time kill tests performed on the solutions of the four formulations at a 30 second contact time:

TABLE 3

| Formulation | pH of 10% solution | Test Temp (° C.) | Log Reduction of *S. aureus* |
|---|---|---|---|
| 2A | 8.6 | 40 | 3.41 |
| 2B | 12.1 | 40 | 1.85 |
| 2C | 8.6 | 25 | 1.88 |
| 2D | 12.1 | 25 | 1.74 |

The above results illustrate that the soap bars in accordance with various aspects of the present invention, that is, soap bars of C8 and C10 soaps formed to comprise an amount of free fatty acid such that the pH of a 10% aqueous solution of the soap bar has a pH no greater than about 9, exhibit substantially higher antibacterial effectiveness than soap bars of C8 and C10 soaps with less free fatty acid. Comparing Formulation 2A and 2B (both tested at 40° C.), Formulation 2A exhibited a log reduction of greater than 3, while Formulation 2B exhibited a log reduction of less than 2.

The above test results also demonstrate that the soap bars formed in accordance with the present invention work particularly well at temperatures at which consumers are generally likely to use the soap bars for body cleansing. Comparing Formulations 2A and 2C, each with a pH of 8.6, Formulation 2A tested at 40° C. exhibited a log reduction of greater than 3, while Formulation 2C tested at 25° C. exhibited a log reduction less than 2.

As should now be appreciated, soap bars in accordance with the various embodiments of the present invention evidence enhanced antibacterial effectiveness due to the composition of the soap components comprising the soap bars, separate and distinct from any added antibacterial agent. Accordingly the soap bars in accordance with various embodiments of the present invention may constitute effective, yet low-cost, antibacterial soap bars.

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential features or elements of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

We claim:

1. A soap bar that exhibits antibacterial effectiveness comprising by weight:

at least about 45% soap having alkyl chain lengths of 8–10 carbon atoms;

a hydric solvent;

water; and free fatty acid such that the pH of a 10% aqueous solution of the soap bar is no greater than about 9.5.

2. The soap bar of claim 1, wherein the soap bar comprises at least about 50% soap having alkyl chain lengths of 8–10 carbon atoms.

3. The soap bar of claim 1, wherein the soap bar comprises free fatty acid such that the pH of a 10% aqueous solution of the soap bar is not greater than about 9.

4. The soap bar of claim 1, wherein said soap comprises a mixture of soap molecules having alkyl chain lengths of 8 carbon atoms and soap molecules having alkyl chain lengths of 10 carbon atoms.

5. The soap bar of claim 4, wherein said mixture comprises approximately 50% soap molecules having alkyl chain lengths of 8 carbon atoms and 50% soap molecules having alkyl chain lengths of 10 carbon atoms.

6. The soap bar of claim 1, wherein said free fatty acid has alkyl chain lengths of 8–10 carbon atoms.

7. The soap bar of claim 1, the soap bar further comprising a polyhydric solvent.

8. The soap bar of claim 5, wherein said polyhydric solvent is selected from the group comprising propylene glycol, dipropylene glycol, butylene glycol, ethylene glycol, 1,7-heptanediol, monoethylene glycols, polyethylene glycols, polypropylene glycols of up to 8,000 molecular weight; mono-C1–4 alkyl ethers of the foregoing, glycerine, any sugar alcohol, and mixtures thereof.

9. The soap bar of claim 1, the soap bar further comprising optional ingredients selected from the group comprising dyes, fragrances, pH adjusters, preservatives, stabilizers, colorants, chelating agents, polymers, gums, and antibacterial active agents.

10. The soap bar of claim 1, wherein the soap bar comprises no more than about 1.5%, by weight, soap having alkyl chain lengths of 12–16 carbon atoms.

11. The soap bar of claim 10, wherein the soap bar comprises no more than about 1%, by weight, soap having alkyl chain lengths of 12–16 carbon atoms.

12. The soap bar of claim 1, wherein soap molecules having alkyl chain lengths of 12–16 carbon atoms are absent from the soap bar.

13. The soap bar of claim 1, wherein the soap bar further comprises no more than about 5%, by weight, soap having alkyl chain lengths of no less than 18 carbon atoms.

14. The soap bar of claim 1, wherein the soap bar comprises about 10% to about 30% of said hydric solvent.

15. The soap bar of claim 14, wherein the soap bar comprises about 20% of said hydric solvent.

16. The soap bar of claim 14, wherein said hydric solvent is propylene glycol.

17. A soap bar comprising, by weight:

at least about 45% soap having alkyl chain lengths of 8–10 carbon atoms;

wherein the soap bar exhibits a log reduction against Gram positive bacteria of at least 3 after 30 seconds of contact at 40° C., as measured against *S. aureus.*

18. The soap bar of claim 14, the soap bar comprising at least about 50% soap having alkyl chain lengths of 8–10 carbon atoms.

19. The soap bar of claim 14, wherein the soap bar further exhibits a log reduction against Gram negative bacteria of at least 3 after 30 seconds of contact at 40° C., as measured against *E. coli.*

20. The soap bar of claim 14, wherein said soap comprises a mixture of soap molecules having alkyl chain lengths of 8 carbon atoms and soap molecules having alkyl chain lengths of 10 carbon atoms.

21. The soap bar of claim 20, wherein said mixture comprises approximately 50% soap molecules having alkyl chain lengths of 8 carbon atoms and 50% soap molecules having alkyl chain lengths of 10 carbon atoms.

22. The soap bar of claim 14, wherein the soap bar further comprises free fatty acid having alkyl chain lengths of 8–10 carbon atoms.

23. The soap bar of claim 14, wherein the soap bar further comprises no more than about 1.5%, by weight, soap having alkyl chain lengths of 12–16 carbon atoms.

24. The soap bar of claim 23, the soap bar comprising no more than 1%, by weight, soap having alkyl chain lengths of 12–16 carbon atoms.

25. The soap bar of claim 14, wherein the soap bar further comprises no more than about 5%, by weight, soap having alkyl chain lengths of no less than 18 carbon atoms.

26. A method of making a soap bar that exhibits antibacterial effectiveness comprising by weight:

at least about 45% soap having alkyl chain lengths of 8–10 carbon atoms; and water;

wherein said process comprises:

combining a neutralizing agent and fatty acids having alkyl chain lengths of 8–10 carbon atoms to form a soap solution;

manipulating the composition of said soap solution, if necessary, so that a pH of a 10% aqueous solution of the soap bar is no greater than about 9.5;

removing a portion of water from said soap solution;

optionally, adding adjuvant ingredients to said soap solution; and solidifying to form the soap bar.

27. The process of claim 26, wherein said manipulating comprises at least one of adding additional neutralizing agent and adding free fatty acid to said soap solution.

28. The process of claim 26, wherein said manipulating comprises manipulating so that a pH of a 10% aqueous solution of the soap bar is no greater than about 9.0.

29. The process of claim 26, wherein said adding free fatty acid comprises adding free fatty acid having alkyl chain lengths of 8–10 carbon atoms.

30. The process of claim 26, wherein said combining a neutralizing agent and fatty acid comprises:

adding a neutralizing agent to a polyhydric solvent;

causing said neutralizing agent and said polyhydric solvent to have a temperature of approximately 80° C. to 90° C.; and adding said fatty acid.

31. A soap bar that exhibits enhanced antibacterial effectiveness comprising, by weight, at least about 50% soap having alkyl chain lengths of 8–10 carbon atoms.

32. The soap bar of claim 31, wherein said soap bar comprises no more than about 1%, by weight, soap having alkyl chain lengths of 12–16 carbon atoms.

33. The soap bar of claim 31, wherein soap molecules having alkyl chain lengths of 12–16 carbon atoms are absent from the soap bar.

34. The soap bar of claim 31, wherein said soap bar further comprises no more than about 5%, by weight, soap having alkyl chain lengths of no less than 18 carbon atoms.

* * * * *